United States Patent
Ametamey et al.

(10) Patent No.: US 10,227,308 B2
(45) Date of Patent: Mar. 12, 2019

(54) RADIOLABELED CANNABINOID RECEPTOR 2 LIGAND

(71) Applicants: Hoffmann-La Roche Inc., Little Falls, NJ (US); EIDGENÖSSISCHE TECHNISCHE HOCHSCHULE ZÜRICH, Zürich (CH); UNIVERSITÄT ZÜRICH, Zürich (CH)

(72) Inventors: Simon M. Ametamey, Zurich (CH); Juergen Fingerle, Kandern (DE); Luca Gobbi, Buus (CH); Uwe Grether, Efringen-Kirchen (DE); Ahmed Haider, Zug (CH); Thomas Hartung, Loerrach (DE); Linjing Mu, Lenzburg (CH); Leo Nicholls, Leeds (GB); Mark Rogers-Evans, Bottmingen (CH); Christoph Ullmer, Fischingen (DE)

(73) Assignees: HOFFMANN-LA ROCHE INC., Little Falls, NJ (US); EIDGENÖSSISCHE TECHNISCHE HOCHSCHULE ZÜRCIH, Zurich (CH); UNIVERSITÄT ZÜRICH, Zurich (CH)

( * ) Notice: Subject to any disclaimer, the term of this patent is extended or adjusted under 35 U.S.C. 154(b) by 0 days.

(21) Appl. No.: 15/443,894

(22) Filed: Feb. 27, 2017

(65) Prior Publication Data

US 2017/0166534 A1 Jun. 15, 2017

Related U.S. Application Data

(63) Continuation of application No. PCT/EP2015/074557, filed on Oct. 23, 2015.

(30) Foreign Application Priority Data

Oct. 27, 2014 (EP) ..................................... 14190523

(51) Int. Cl.
| | |
|---|---|
| *C07D 231/40* | (2006.01) |
| *G01N 33/566* | (2006.01) |
| *A61K 51/04* | (2006.01) |
| *C07B 59/00* | (2006.01) |
| *G01N 33/60* | (2006.01) |
| *G01N 33/94* | (2006.01) |

(52) U.S. Cl.
CPC ........ *C07D 231/40* (2013.01); *A61K 51/0453* (2013.01); *C07B 59/002* (2013.01); *G01N 33/566* (2013.01); *G01N 33/60* (2013.01); *G01N 33/948* (2013.01); *G01N 2333/705* (2013.01); *G01N 2333/726* (2013.01); *G01N 2500/20* (2013.01); *G01N 2800/00* (2013.01)

(58) Field of Classification Search
CPC .............................. C07D 231/40; G01N 33/60
See application file for complete search history.

(56) References Cited

U.S. PATENT DOCUMENTS

2010/0069348 A1   3/2010   Carroll et al.

FOREIGN PATENT DOCUMENTS

| WO | 2008/141249 A1 | 11/2008 |
| WO | 2011/061744 A2 | 5/2011 |
| WO | 2011/061744 A3 | 5/2011 |
| WO | 2016/066534 A1 | 6/2016 |

OTHER PUBLICATIONS

Akhmetshina et al., "The cannabinoid receptor CB2 exerts antifibrotic effects in experimental dermal fibrosis" Arthritis Rheum 60(4):1129-1136 ( 2009).
Ashton et al., "The cannabinoid CB2 receptor as a target for inflammation-dependent neurodegeneration" Current Neuropharmacol ((Abstract only)), 5:73-80 ( 2007).
Bab et al., "Cannabinoid receptors and the regulation of bone mass" Br J Pharmacol 153:182-188 ( 2008).
Batkai et al., "Cannabinoid-2 receptor mediates protection against hepatic ischemia/reperfusion injury" FASEB J 21:1788-1800 ( 2007).
Beltramo et al., "Cannabinoid type 2 receptor as a target for chronic—pain" Mini-Reviews in Medicinal Chemi 9:11-25 ( 2009).
Cabral et al., "Cannabinoid receptors in microglia of the central nervous system: immune functional relevance" J Leukocyte Biol 78:1192-1197 ( 2005).
Cabral et al., "CB $_2$ receptors in the brain: role in central immune function" Br J Pharmacol 153:240-251 ( 2008).
Centonze et al., "The endocannabinoid system in peripheral lymphocytes as a mirror of neuroinflammatory diseases" Curr Pharmaceutcal Des 14:2370-2382 ( 2008).
International Preliminary Report on Patentability for International Patent Application PCT/EP2015/074557 dated Sep. 20, 2016.

(Continued)

*Primary Examiner* — Zohreh A Fay
(74) *Attorney, Agent, or Firm* — Zong-Qiang Bill Tian

(57) ABSTRACT

The present invention relates to a compound of formula (I)

(I)

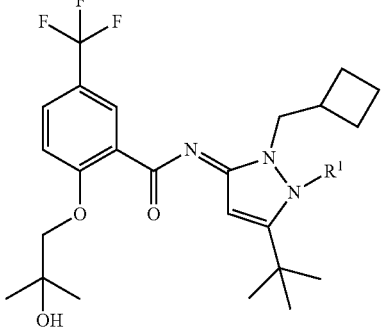

Figure 1:
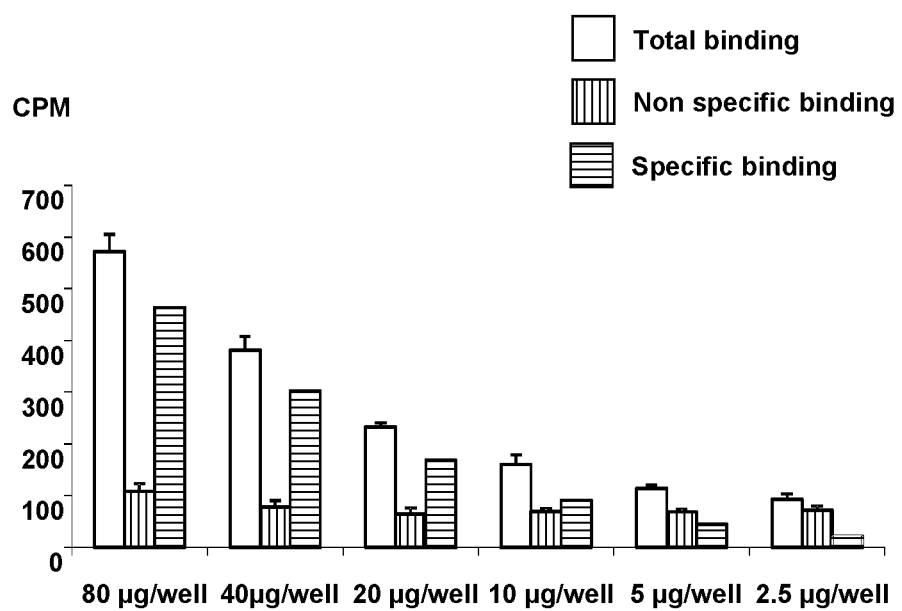

wherein R[1] is defined as in the description and in the claims. The compound of formula (I) can be used as radiolabeled ligand.

8 Claims, 3 Drawing Sheets

(56) References Cited

OTHER PUBLICATIONS

Written Opinion of the International Searching Authority for International Patent Application No. PCT/EP2015/074557 dated Dec. 22, 2015.

Defer et al., "The cannabinoid receptor type 2 promotes cardiac myocyte and fibroblast survival and protects against ischemia/reperfusion-induced cardiomyopathy" FASEB J 23:2120-2130 ( 2009).

Evens et al., "Synthesis and biological evaluation of carbon-11- and fluorine-18-labeled 2-oxoquinoline derivatives for type 2 cannabinoid receptor positron emission tomography imaging" Nuclear Medicine and Biology 36(4):455-465 (May 1, 2009).

Feizi et al., "The preventive effect of cannabinoids on reperfusion-induced ischemia of mouse kidney" Experimental and Toxicologic Pathol 60:405-410 ( 2008).

Garcia-Gonzalez et al., "Cannabinoids inhibit fibrogenesis in diffuse systemic sclerosis fibroblasts" Rheumatology 48:1050-1056 ( 2009).

Julien et al., "Antifibrogenic role of the cannabinoid receptor CB2 in the liver" Gastroenterology 128:742-755 ( 2005).

Lotersztajn et al., "CB2 receptors as new therapeutic targets for liver diseases" Br J Pharmacol 153:286-289 ( 2008).

Lotersztajn et al., "Le systeme cannabinoide: perspectives therapeutiques au cours des hepatopathies chroniques" Gastroenterol Clin Biol 31:255-258 ( 2007).

Mach et al., "The role of the endocannabinoid system in atherosclerosis" J Neuroendocrinol 20( Suppl 1):53-57 ( 2008).

Mallat et al., "Cannabinoid receptors as new targets of antifibrosing strategies during chronic liver diseases" Expert Opin Ther Targets 11(3):403-409 ( 2007).

Miller et al., "$CB^2$ receptor-mediated migration of immune cells: it can go either way" Br J Pharmcol 153:299-308 ( 2008).

Mu et al., "Radiolabeling and in vitro/in vivo evaluation of N-(1-adamantyl)-8-methoxy-4-oxo-1-phenyl-1,4-dihydroquinoline-3-carboxamide as a PET probe for imaging cannabinoid type 2 receptor" J Neurochem 126(5):616-624 (Sep. 19, 2013).

Mu et al., "Synthesis and preliminary evaluation of a 2-oxoquinoline carboxylic acid derivative for PET imaging the Cannabinoid type 2 receptor" Pharmaceuticals 7:339-352 ( 2014).

Munoz-Luque et al., "Regression of fibrosis after chronic stimulation of cannabinoid CB2 receptor in cirrhotic rats" J Pharmacol Exper Ther 324(2):475-483 ( 2008).

Pacher et al., "Endocannabinoids and cannabinoid receptors in ischaemia-reperfusion injury and preconditioning" Br J Pharmacol 153:252-262 ( 2008).

Priller et al., "Mead ethanolamide, a novel eicosanoid, is an agonist for the central (CB1) and peripheral (CB2) cannabinoid receptors" Am Society Pharmacol Exper Ther 48:288-292 ( 1995).

Wright et al., "Cannabinoid $CB_2$ receptors in the gastrointestinal tract: a regulatory system in states of inflammation" Br J Pharmacol 153:263-270 ( 2008).

Yang et al., "Inhibition of hepatic tumour necrosis factor-α attenuates the anandamide-induced vasoconstrictive response in cirrhotic rat livers" Liver International 29(5):678-685 ( 2009).

Zhang et al., "Cannabinoid $CB_2$ receptor activation decreases cerebral infarction in a mouse focal ischemia/reperfusion model" J Cerebral Blood Flow Metab 27:1387-1396 ( 2007).

RADIOLABELED CANNABINOID RECEPTOR 2 LIGAND

CROSS REFERENCE TO RELATED APPLICATIONS

This application is a continuation of International Application No. PCT/EP2015/074557 having an International Filing Date of 23 Oct. 2015, the entire contents of which are incorporated herein by reference, and which claims the benefit of priority under 35 U.S.C. § 119 to EP 14190523.2 filed 27 Oct. 2014.

FIELD OF THE INVENTION

The present invention relates to a radiolabeled Cannabinoid Receptor 2 ligand.

SUMMARY OF THE INVENTION

The invention relates in particular to a compound of formula (I)

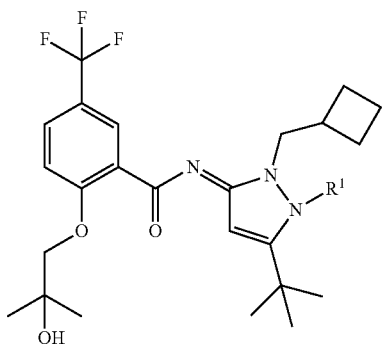

(I)

wherein $R^1$ is a methyl group and wherein said methyl group comprises at least one radionuclide.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor has a wide range of expression. It is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages, B- and, T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also present in the brain where it is found primarily on microglia and not on neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2, might be involved in pre-conditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The need to unequivocally detect CB2 in tissues came along the growing interest in this receptor. Assessing CB2 expression and receptor occupancy in patients or samples with appropriate tools could verify the target cell of expression, permit dose finding of any CB2 ligand in human studies, or be used for diagnostic purpose.

There is up to now a deficit in efficient tools for the detection of CB2 receptor protein in tissues, which is a consequence of the low expression levels of the CB2 receptor. Another reason for the lack of specific antibodies as detection tools of CB2 could be reasoned in the apparent difficulty to use CB2 as an immunogen.

In order to approach this problem, we explored the possibility of using a radiolabeled ligand that selectively binds to CB2. To our knowledge, there is only one radiolabeled CB2 ligand available, called [$^3$H]-CP55940 (Priller, J. et al Molecular Pharmacology 1995, 48, 288-292). However [$^3$H]-CP55940 is a non-selective agonist for CB1 and CB2 receptors and does not distinguish between the two receptors in several mammalian species tested. Therefore, in order to detect CB2 in tissues that might also express CB1, there is a need for a selective CB2 ligand that is radiolabeled with the common isotopes $^3$H for competition assays, $^{14}$C for autoradiography or $^{11}$C for PET tracing techniques.

The first strategy was to identify ligands with high selectivity for CB2 versus CB1 and structural homology to naturally occurring cannabinoids. The CB2 agonist HU-910 (described in WO 2011/061744) was selected according to its high selectivity and to its structurally related nature to cannabinoid type compounds found in plants. Although HU-910 selectively and competitively binds to CB2 receptors that have been labeled with [$^3$H]-CP55940, [$^3$H]-HU-910 displayed high non-specific binding thereby masking the specific binding sites to CB2 receptors that are expected to represent a small fraction of the total binding sites. Without willing to be bound by this theory, we ascribed this phenomenon to the high lipophilicity of [$^3$H]-HU-910, causing a high partitioning into the membranes and thereby causing a high non-specific binding that cannot be competed off by excess of unlabeled HU-910.

It was therefore desired to find a CB2 ligand of high hydrophilicity in addition to potency and selectivity, paired with the option to introduce a radiolabel in a final step of the chemical synthesis.

The compound of formula (I) as defined above was surprisingly identified to have the desired properties and turned with highly reduced non-specific binding.

The compound of formula (I) proved to specifically and selectively bind to membranes prepared from cells recombinantly expressing CB2 receptors. Furthermore, the compound of formula (I) turned out to specifically label CB2 receptors in spleen tissues, which is an organ with a high expression of both CB1 and CB2 receptors. Moreover, in spleen tissues isolated from CB2 receptor deficient mice, binding by the compound of formula (I) was absent. In this particular case, the total binding signal could not be reduced by excess of unlabeled ($R^1$=$CH_3$) compound of formula (I).

The compound of formula (I) can therefore be used for example in tissue autoradiography and PET imaging, e.g. to assess receptor expression and receptor occupancy, for dose finding of any CB2 ligand in human studies, or for diagnostic purposes.

In the present description, the term "radionuclide" defines the isotope of an atom with an unstable nucleus and that undergoes radioactive decay. Particular radionuclides of the invention are [$^3$H], [$^{11}$C] and [$^{14}$C].

The term "binding constant" refers to the equilibrium constant associated with the binding reaction of a ligand to a receptor.

The term "selective binding" characterizes the binding of a ligand to a very limited type of receptors.

The invention thus relates to:

A compound of formula (I) wherein the at least one radionuclide is independently selected from [$^3$H], [$^{11}$C] and [$^{14}$C];

A compound of formula (I) wherein $R^1$ is C[$^3$H]$_3$, [$^{11}$C]H$_3$ or [$^{14}$C]H$_3$;

A compound of formula (I) selected from (NE)-N-[5-tert-butyl-2-(cyclobutylmethyl)-1-(tritritiomethyl)pyrazol-3-ylidene]-2-(2-hydroxy-2-methyl-propoxy)-5-(trifluoromethyl)benzamide;

(NE)-N-[5-tert-butyl-2-(cyclobutylmethyl)-1-([$^{14}$C]methyl)pyrazol-3-ylidene]-2-(2-hydroxy-2-methyl-propoxy)-5-(trifluoromethyl)benzamide; and (NE)-N-[5-tert-butyl-2-(cyclobutylmethyl)-1-([$^{11}$C]methyl)pyrazol-3-ylidene]-2-(2-hydroxy-2-methyl-propoxy)-5-(trifluoromethyl)benzamide;

The use of a compound of formula (I) for localizing a CB2 receptor in a patient or sample;

The use of a compound of formula (I) for imaging a CB2 receptor in a patient or sample;

The use of a compound of formula (I) for determining whether another compound binds to a CB2 receptor;

The use of a compound of formula (I) for determining whether another compound binds to a CB2 receptor further comprising measuring the binding constant of said another compound to the CB2 receptor;

The use as defined above in the presence of the CB1 receptor;

The use of a compound of formula (I) to determine whether a disease is characterized by a change in the expression of the CB2 receptor;

The use of a compound of formula (I) to determine whether a disease is characterized by a change in the expression of the CB2 receptor, wherein the disease is pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

A compound of formula (I) for use in the diagnosis in a patient or tissue of a disease;

A compound of formula (I) for use in the diagnosis in a patient or tissue of a disease as defined above, wherein the disease is characterized by a change in the expression of the CB2 receptor in said patient or tissue compared to the expression of the CB2 receptors in a healthy subject or tissue;

A compound for use as defined above wherein the diagnosis comprises the step of comparing the expression of the CB2 receptor in the patient or tissue to the expression of the CB2 receptor in a healthy subject or tissue;

The use of a compound of formula (I) to predict whether a patient affected with a disease is likely to respond to a treatment involving the administration of a CB2 ligand;

The use of a compound of formula (I) to predict whether a patient affected with a disease is likely to respond to a treatment involving the administration of a CB2 ligand comprising comparing the expression of the CB2 receptor in the patient to the expression of the CB2 receptor in a healthy subject or tissue; and The use of a compound of formula (I) for determining the dose of a CB2 ligand that needs to be administered to a patient in need thereof.

The invention further relates to a method for identifying a compound that binds to a CB2 receptor comprising the following steps:
(a) contacting the compound suspected to bind to the CB2 receptor with a sample comprising a CB2 receptor and a compound of formula (I); and
(b) monitoring whether the compound suspected to bind to the CB2 receptor influences the binding of the compound of formula (I) to the CB2 receptor.

The invention also relates to a method as defined above, further comprising the step of measuring the binding strength to the CB2 receptor of the compound suspected to bind to the CB2 receptor.

The invention also relates to a method for determining whether a compound selectively binds to the CB2 receptor against the CB1 receptor comprising the following steps:
(a) contacting the compound suspected to bind selectively to the CB2 receptor with a sample comprising the CB1 receptor, the CB2 receptor and a compound of formula (I); and
(b) monitoring whether the compound suspected to bind selectively to the CB2 receptor influences the binding of the compound of formula (I) to the CB2 receptor.

The invention further relates to a method for determining whether a compound selectively binds to the CB2 receptor against the CB1 receptor as defined above further comprising measuring the binding constant to the CB2 receptor of the compound suspected to bind selectively to the CB2 receptor.

The invention also relates to a method for identifying a cellular receptor as a CB2 receptor comprising the following steps:
(a) contacting a sample suspected to comprise a CB2 receptor with a compound of formula (I); and
(b) monitoring whether the binding of the compound of formula (I) has occurred; and
(c) optionally further contacting the sample with another known CB2 ligand and monitoring whether said known CB2 ligand has displaced the compound of formula (I) from its binding site.

The invention also relates to a method for measuring in an animal, a patient or a sample the percentage of CB2 receptors occupied by a compound suspected to bind to the CB2 receptor when a dose of said compound is administered to the animal or patient, or put in contact with the sample, comprising the following steps:
(a) administering to an animal or patient or contacting a sample comprising at least one CB2 receptor with a compound of formula (I) in an amount sufficient to occupy 100% of the CB2 receptors of the animal, patient or sample;
(b) administering to the animal or patient or contacting the sample with the dose of said compound suspected to bind to the CB2 receptor;
(c) monitoring the displacement of the compound of formula (I) by the compound suspected to bind to the CB2 receptor; and
(d) calculating the percentage of the at least one CB2 receptor that is occupied by the compound suspected to bind to the CB2 receptor.

The invention also relates to a method for determining the dose of a CB2 ligand that needs to be administered to a patient in need thereof comprising the following steps:
(a) determining in an animal or sample the percentage of CB2 receptors occupied by the CB2 ligand after a dose of the CB2 ligand that is known to provide a pharmacological response in said animal or sample is administered to the animal or put in contact with the sample comprising:
(a1) administering to the animal or contacting the sample with a compound of formula (I) in an amount sufficient to occupy 100% of the CB2 receptors of the animal or sample;
(a2) administering to the animal or contacting the sample with the dose that is known to provide the pharmacological response in said animal or sample;
(a3) monitoring the displacement of the compound of formula (I) by the CB2 ligand; and
(a4) calculating the percentage of CB2 receptors that is occupied by the CB2 ligand;
(b) determining the dose of the CB2 ligand that gives the same percentage of CB2 receptors occupied by the CB2 ligand in a human subject or sample comprising:
(b1) administering to the human subject or contacting the sample with a compound of formula (I) in an amount sufficient to occupy 100% of the CB2 receptors of the human subject;
(b2) administering to the human subject or contacting the sample with a dose of the CB2 ligand;
(b3) monitoring the displacement of the compound of formula (I) by the CB2 ligand; and
(b4) calculating the percentage of CB2 receptors that is occupied by the CB2 ligand;
(b5) repeating steps (b2) to (b4) until the percentage of CB2 receptors calculated in step (a4) is also obtained in step (b4); and
(b6) calculating the addition of the doses that have been administered in steps (b2) in order to obtain the dose of the CB2 ligand that needs to be administered to a patient.

The invention also relates to a method for determining whether a disease is characterized by a change in the expression of the CB2 receptor comprising the following steps:
(a) contacting a sample or administering to a subject affected with said disease and a healthy sample or a healthy subject with a compound of formula (I);
(b) monitoring in both samples whether the binding of the compound of formula (I) has occurred; and (c) comparing in both samples the amount of compound of formula (I) that is bound to the CB2 receptors.

The invention also relates to a method of the invention wherein autoradiography or positron emission tomography is used during the monitoring.

The invention further relates to a pharmaceutical composition comprising a compound of formula (I).

The invention also relates to a compound of formula m for use as a diagnostic agent, i.e. for use in the diagnostic of a disease.

The invention also relates to a compound of formula (I) for use in the diagnostic of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

The synthesis of the compound of formula (I) can, for example, be accomplished according to the following scheme.

The target compound is easily accessible via one-step tritio-methylation reaction of the desmethyl precursor N-[5-tert-butyl-2-(cyclobutylmethyl)pyrazol-3-yl]-2-(2-hydroxy-2-methyl-propoxy)-5-(trifluoromethyl)benzamide using well established tritio-methylation agents like [$^3$H]methyl sulfonates (e.g., [$^3$H]methyl 4-nitrobenzenesulfonate) or [$^3$H]methyl iodide. The main advantage of this synthesis concept is that the incorporation of the radionuclide can be accomplished in the last step of the synthesis route which is usually the most feasible method to fulfill the fundamental principle of radiation protection known as ALARA (as low as reasonably achievable).

In order to further minimize the use of radioactive material the desmethyl-precursor is typically used in 2-3 fold excess in relation to the radio-methylation agent.

By applying the same synthesis concept and by using known [$^{14}$C/$^{11}$C]-labeled methyl transfer reagents like [$^{14}$C/$^{11}$C]MeI or [$^{14}$C/$^{11}$C]methylsulfonates (e.g., [$^{14}$C/$^{11}$C] methyl triflate, [$^{14}$C/$^{11}$C]methyl 4-nitrobenzenesulfonate) the corresponding [$^{14}$C]- and [$^{11}$C]-labeled derivatives can be prepared starting from the same precursor molecule.

In particular for [$^{11}$C]-labeling strategies it is of utmost importance to establish a short, fast and efficient synthesis due to the short half-life of 20 min of the positron emitter carbon-11.

Scheme 1

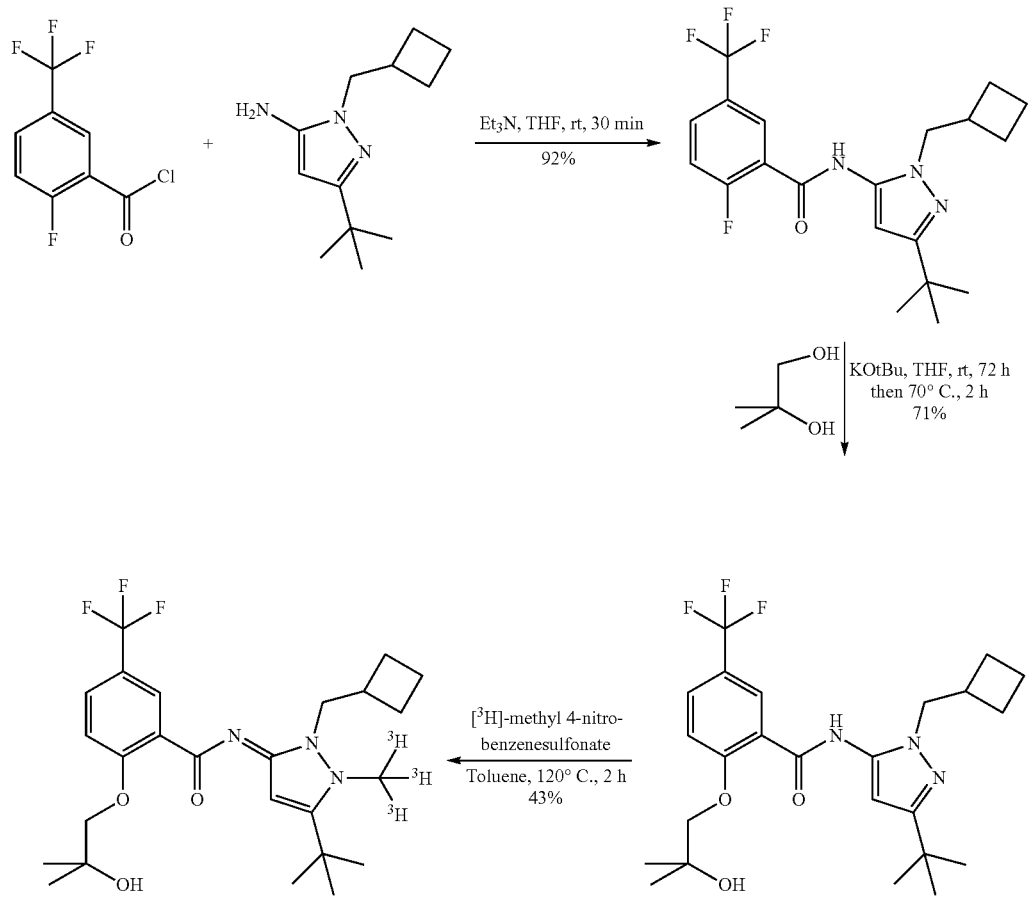

The invention thus also relates to a process for the manufacture of a compound of formula (I) comprising reacting a compound of formula (A)

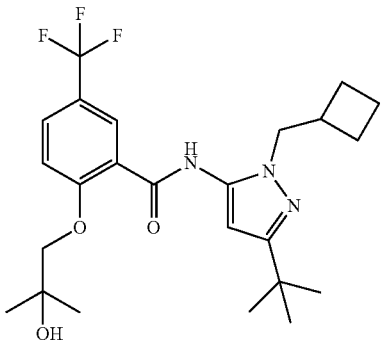

in the presence of [$^3$H]-methyl 4-nitrobenzenesulfonate, [$^3$H]-methyl iodide, [$^{11}$C]-methyl triflate, [$^{11}$C]-methyl iodide, [$^{11}$C]-methyl 4-nitrobenzenesulfonate, [$^{14}$C]-methyl triflate, [$^{14}$C]-methyl iodide or [$^{14}$C]-methyl 4-nitrobenzenesulfonate.

In the process of the invention, the compound of formula (A) is advantageously reacted in the presence of [$^3$H]-methyl 4-nitrobenzenesulfonate, [$^{11}$C]-methyl triflate or [$^{14}$C]-methyl 4-nitrobenzenesulfonate The process of the invention is advantageously carried out in toluene.

The process of the invention is advantageously carried out at a temperature of approximately 100° C. to 150° C., particularly at approximately 120° C.

The invention further relates to a compound manufactured according to a process of the invention.

The invention will now be illustrated by the following examples which have no limiting character.

EXAMPLES

Abbreviations
CAN=CAS Registry Number; LC=liquid chromatography; MS=mass spectrometry; NMR=nuclear magnetic resonance; SEM=standard error of the mean; THF=tetrahydrofuran; WT=wild type.

Experimental

All reactions were undertaken in flame dried glassware under an atmosphere of argon. Analytical grade solvents were used for reactions and when required, dry solvents were used without further purification. Reagents were purchased from reputable commercial suppliers and used without further purification, unless otherwise stated. All $^1$H NMR spectra were recorded on a Bruker Advance Ultra Shield 300 MHz spectrometer. Chemical shifts are reported relevant to the stated deuterated solvent. Mass spectra were recorded on PE Sciex API 150EX LC/MS Turbo Spray System. Flash chromatography was conducted using an Isco Combi Flash companion, using prepacked silica columns (230-400 mesh, 40-63 μm) of various sizes from various commercial suppliers. Thin layer chromatography was carried on pre-coated plates (20×20 cm, silica gel F254) purchased from Merck KgaA and was visualized using a 254 nm CAMAG UV lamp or using a basic potassium permanganate solution. All reactions were monitored using a combination of thin layer chromatography, LCMS and $^1$H NMR.

Example 1 (NE)-N-[5-tert-butyl-2-(cyclobutylmethyl)-1-(tritritiomethyl)pyrazol-3-ylidene]-2-(2-hydroxy-2-methyl-propoxy)-5-(trifluoromethyl)benzamide

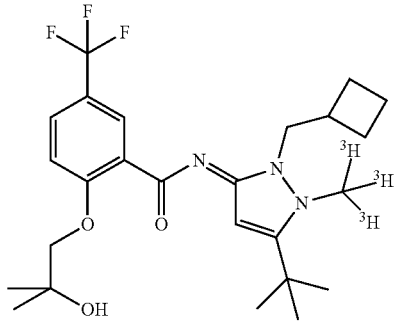 [SMILES: [3H]C([3H])([3H])n1c(C(C)(C)C)c/c(=N\C(=O)c2cc(C(F)(F)F)ccc2OCC(C)(C)O)n1CC1CCC1]

a) N-[5-tert-butyl-2-(cyclobutylmethyl)pyrazol-3-yl]-2-fluoro-5-(trifluoromethyl)benzamide

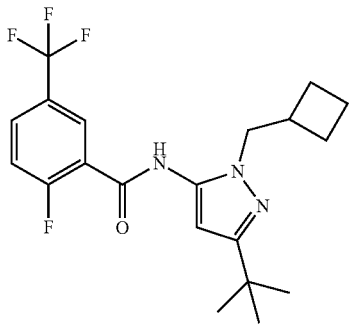 [SMILES: CC(C)(C)c1cc(NC(=O)c2cc(C(F)(F)F)ccc2F)n(CC2CCC2)n1]

To a solution of 3-tert-butyl-1-(cyclobutylmethyl)-1H-pyrazol-5-amine (458 mg, 2.21 mmol, CAN 1018679-74-7) and triethylamine (670 mg, 923 μL, 6.62 mmol) in dry THF (9 mL) was added dropwise a solution of 2-fluoro-5-(trifluoromethyl)benzoyl chloride (500 mg, 333 μL, 2.21 mmol, CAN 207981-46-2) in dry THF (9 mL). The pink suspension was stirred at ambient temperature for 30 minutes and extracted with 1M aqueous sodium hydrogen carbonate solution (70 mL). The aqueous layer was extracted with ethyl acetate (3×70 mL). The organic layers were combined and dried using sodium sulfate, before concentrating in vacuo. The crude material was purified by flash chromatography (10% to 20% ethyl acetate in heptane) to give 794.4 mg (2.0 mmol, 91% yield) of the title compound as an orange powder.

$^1$H NMR (300 MHz, CHLOROFORM-d) δ ppm 1.32 (s, 9H), 1.72-2.20 (m, 6H), 2.81 (dt, J=14.73, 7.37 Hz, 1H), 4.04 (d, J=7.06 Hz, 2H), 6.37 (s, 1H) 7.38 (dd, J=11.61, 8.58 Hz, 1H), 7.80-7.91 (m, 1H), 8.27 (d, J=15.95 Hz, 1H), 8.53 (dd, J=6.96, 2.32 Hz, 1H). MS m/z 398.2 [M+H]$^+$.

b) N-[5-tert-butyl-2-(cyclobutylmethyl)pyrazol-3-yl]-2-(2-hydroxy-2-methyl-propoxy)-5-(trifluoromethyl)benzamide

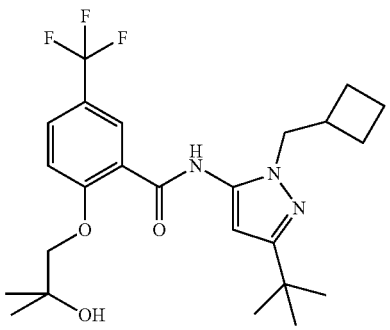 [SMILES: CC(C)(O)COc1ccc(C(F)(F)F)cc1C(=O)Nc1cc(C(C)(C)C)nn1CC1CCC1]

Potassium tert-butoxide (203 mg, 1.81 mmol) was added to an ice-cold solution of 2-methylpropane-1,2-diol (136 mg, 138 μL, 1.51 mmol, CAN 558-43-0) in dry THF (7 mL). The colorless suspension was stirred at 0° C. for 5 minutes, allowed to warm to room temperature and stirred for 1 hour. At 0° C. (N-[5-tert-butyl-2-(cyclobutylmethyl)pyrazol-3-yl]-2-fluoro-5-(trifluoromethyl)benzamide (400 mg, 1.01 mmol) was added. The resulting yellow suspension was stirred at room temperature for 72 h. Potassium tert-butoxide (203 mg, 1.81 mmol) was added and stirring was continued at 70° C. for 2 hours. Aqueous 1M sodium hydrogen carbonate solution (50 mL) and ethyl acetate (50 mL) were added and the layers were separated. The aqueous phase was extracted with ethyl acetate (2×50 mL). The organic layers were combined and dried using sodium sulfate, before concentrating in vacuo. The crude material was purified by flash chromatography (30 to 50% ethyl acetate in heptane), giving 334 mg (0.714 mmol, 71% yield) of the title compound as a white powder.

$^1$H NMR (300 MHz, CHLOROFORM-d) δ ppm 1.30 (s, 9H), 1.43 (s, 6H), 1.69-2.05 (m, 6H), 2.77 (dt, J=14.63, 7.22 Hz, 1H), 4.02-4.19 (m, 4H), 6.19 (s, 1H), 7.13 (d, J=8.88 Hz, 1H), 7.75 (dd, J=8.68, 2.42 Hz, 1H), 8.55 (d, J=2.22 Hz, 1H), 9.69 (s, 1H). MS m/z 468.3 [M+H]$^+$.

c) (NE)-N-[5-tert-butyl-2-(cyclobutylmethyl)-1-(tritritiomethyl)pyrazol-3-ylidene]-2-(2-hydroxy-2-methyl-propoxy)-5-(trifluoromethyl)benzamide In a 1-ml screw cap vial N-[5-tert-butyl-2-(cyclobutylmethyl)pyrazol-3-yl]-2-(2-hydroxy-2-methyl-propoxy)-5-(trifluoromethyl)benzamide (1.0 mg, 2.14 μmmol) was added to a solution of [$^3$H]methyl 4-nitrobenzenesulfonate (50 mCi, 0.16 mg, 0.71 μmmol) in dry toluene (50 μL). The vial was closed and the reaction mixture was stirred for 2 h at 120° C. Afterwards the crude material was purified by flash chromatography (silica, dichloromethane/methanol 95:5) to give 21.4 mCi (43%) of the title compound in >99% radiochemical purity (HPLC: X-Bridge C18, acetonitrile/formate buffer pH 3.0) and in a specific activity of 85 Ci/mmol.

Example 2 (NE)-N-[5-tert-butyl-2-(cyclobutylmethyl)-1-([$^{14}$C]methyl)pyrazol-3-ylidene]-2-(2-hydroxy-2-methyl-propoxy)-5-(trifluoromethyl)benzamide

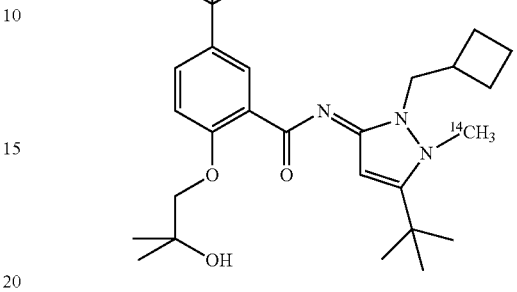

In a 2-ml screw cap vial N-[5-tert-butyl-2-(cyclobutylmethyl)pyrazol-3-yl]-2-(2-hydroxy-2-methyl-propoxy)-5-(trifluoromethyl)benzamide (209 mg, 0.45 mmol) was added to a solution of [14C]methyl 4-nitrobenzenesulfonate (25 mCi, 98 mg, 0.45 mmol) in dry toluene (1.5 mL). The vial was closed and the reaction mixture was stirred for 20 h at 120° C. After removal of the solvent the crude material was purified by flash chromatography (silica, dichloromethane/methanol/triethylamine 97:3:0.5) to give 8.7 mCi (35%) of the title compound in >99% radiochemical purity (HPLC: X-Bridge C18, water/acetonitrile containing 0.05% of triethylamine) and in a specific activity of 56 mCi/mmol.

Example 3 (NE)-N-[5-tert-butyl-2-(cyclobutylmethyl)-1-([$^{11}$C]methyl)pyrazol-3-ylidene]-2-(2-hydroxy-2-methyl-propoxy)-5-(trifluoromethyl)benzamide

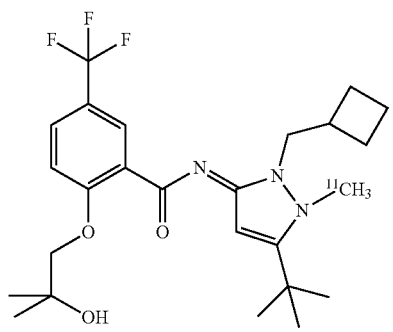 [SMILES: CC(C)(O)COc1ccc(C(F)(F)F)cc1C(=O)/N=c1\cc(C(C)(C)C)n([11CH3])n1CC1CCC1]

Carbon-11 was produced via the $^{14}$N(p,α)$^{11}$C nuclear reaction at a Cyclone 18/9 cyclotron (18-MeV, IBA, Belgium) in the form of [$^{11}$C]CO$_2$. [$^{11}$C]Methyl iodide ([$^{11}$C]MeI) was generated in a 2-step reaction sequence involving the reduction of [$^{11}$C]CO$_2$ over nickel catalyst to [$^{11}$C]methane and subsequent gas phase iodination. After passing through an AgOTf/C column at 190° C., the more reactive [$^{11}$C]methyl triflate (ca. 30 GBq) was formed which was bubbled through a 3-mL reactor vial containing N-[5-tert-butyl-2-(cyclobutyl methyl)pyrazol-3-yl]-2-(2-hydroxy-2-methyl-propoxy)-5-(trifluoromethyl) benzamide (3 mg, 6.46 μmol) and dry toluene (0.25 mL). The mixture was heated to 150° C. for 5 min. After dilution with 30% acetonitrile in water (1.5 mL), the crude product was purified using semi-preparative HPLC (column: Sunfire C18 5 μm; 10×150 mm; product peak at ca. 10 min). The collected product was diluted with water (10 mL), trapped on a C18 cartridge (Waters, preconditioned with 5 mL EtOH and 10 mL water), washed with water (5 mL) and eluted with EtOH (0.5 mL). For formulation of the final product, water for injection (9.5 mL) was added to give an ethanol concentration of 5%. For quality control, an aliquot of the formulated solution was injected into an analytical HPLC system (column: ACE column, C18, 3 μm). The identity of the $^{11}$C-labeled product was confirmed by comparison with the retention time of its nonradioactive reference compound and by co-injection. Specific activity of the product was calculated by comparison of UV peak intensity with a calibration curve of the cold reference compound. In a typical experiment, the specific activity was ≥500 GBq/μmol with a total activity of 2±1.00 GBq at the end of synthesis (n=30). The total synthesis time from end of bombardment was approximately 40 min.

Example 4 Radioligand Binding in Mice

Cell Culture

CHO-K1 beta-arrestin cells (DiscoveRx Inc., Fremont, Calif.) expressing human CB1 and human CB2 were cultured in F-12 Nutrient Mixture (HAM) supplemented with 10% FBS, 300 μg ml-1 hygromycin and 800 μg ml-1 geneticin (G418). Cells were incubated in a humidified atmosphere at 37° C. with 5% CO2.

Radioligand Binding Assay

Stably transfected cells or spleen tissue were homogenized in 15 mmol L-1 Hepes, 0.3 mmol L-1 EDTA, 1 mmol L-1 EGTA, 2 mmol L-1 MgCl$_2$, complete EDTA-free protease inhibitor (Roche Applied Science, Rotkreuz, Switzerland), pH 7.4 using a glass potter and centrifugation at 47,800 g at 4° C. for 30 min. The pellet was then rehomogenized twice in the same buffer and centrifuged (47,800 g, 4° C., 30 min). The final pellet was then resuspended in 75 mmol L-1 Tris, 0.3 mmol L-1 EDTA, 1 mmol L-1 EGTA, 12.5 mmol L-1 MgCl$_2$, 250 mmol L-1 sucrose, pH 7.4 at a protein concentration of 1 to 3 mg mL-1, aliquoted, frozen on dry ice and stored at −80° C.

Saturation Binding

Saturation binding was performed with 0.05 to 2.4 nM compound of formula (I) and 40 μg of membrane protein. CP55940 (10 μM) was used to define nonspecific binding. Assay buffer consisted of 50 mmol L-1 Tris-HCl, 5 mmol L-1 MgCl$_2$, 2.5 mmol L-1 EGTA, and 0.1% fatty acid-free BSA, pH 7.4. Assays were initiated by addition of membranes in a final volume of 250 μl/well. Assays were incubated for 2 h at room temperature and then vacuum filtered and rinsed with wash buffer (50 mmol L-1 Tris-HCl, 5 mmol L-1 MgCl$_2$, 2.5 mmol L-1 EGTA, and 0.5% fatty acid-free BSA, pH 7.4) on a Filtermate cell harvester through Packard GF/B filters presoaked in 0.3% polyethylenimine.

Competition Binding

For competition binding, membrane preparations were incubated either with 0.3 nM of [$^3$H]-CP55940 in the presence or absence of increasing concentrations of unlabeled (R$^1$=CH$_3$) compound of formula (I) or with 1.5 nM compound of formula (I) and increasing amounts of membranes (2.5-80 μg) in the presence or absence of CP55940 (10 μM) for 60 min at 30° C. in a final volume of 0.2 mL of 50 mmol L-1 Tris-HCl, 5 mmol L-1 MgCl$_2$, 2.5 mmol L-1 EGTA, 0.1% fatty acid-free BSA and 1% DMSO, pH 7.4, buffer, gently shaking. All binding reactions were terminated by vacuum filtration onto 0.5% polyethylenimine presoaked GF/B filter plates (Packard) followed by seven brief washes with 2 mL of ice-cold binding buffer containing 0.5% fatty acid-free BSA. Plates were dried at 50° C. for 1 h and liquid scintillation counting was used to determine bound radiolabel. IC50 values and Hill slopes were determined by a four parameter logistic model using ActivityBase (ID Business Solution, Ltd.).

The results are shown in Table 1 below and in FIGS. 1 to 3.

TABLE 1

Radioligand competition binding of [$^3$H]-CP55940 using CHO-K1 cell expressing human CB2 receptors

|  | Human CB1 | Human CB2 |
| --- | --- | --- |
| pKi | 5.41 | 8.97 |
| SEM | ±0.018 | ±0.027 |
| n | 6 | 13 |

Table 1 demonstrates high binding selectivity of the unlabeled (R$^1$=CH$_3$) compound of formula (I) for human CB2 receptors (pKi 8.97) vs human CB1 receptors (pKi 5.41) in cells that recombinantly express these receptors and using the non-selective CB1/CB2 radioligand [$^3$H]-CP55940.

FIG. 1: Radioligand binding (1.5 nM [$^3$H]-compound of formula (I)) using mouse spleen tissue WT FIG. 1 shows high specific binding in mouse spleen tissues of the compound of formula (I). Using increasing amounts of membranes, non-specific binding remains constant but specific binding increases.

Figure 2:
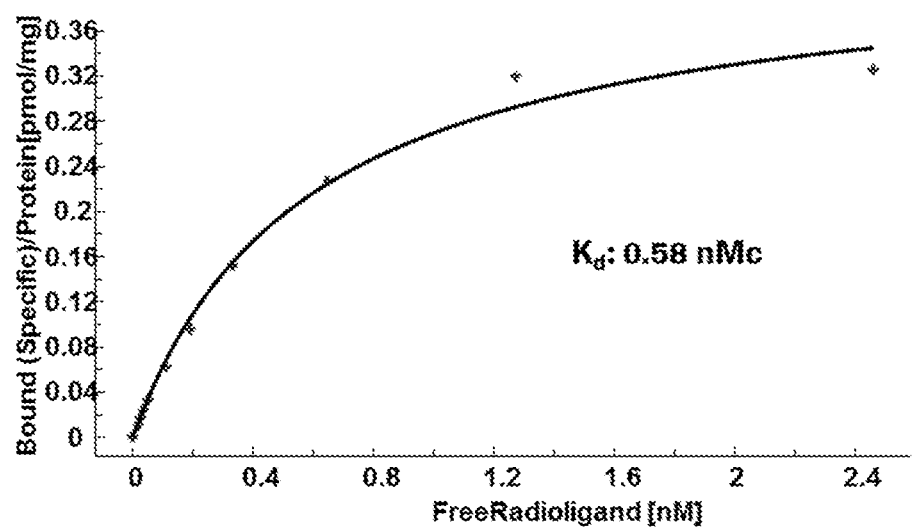

FIG. 2: Radioligand saturation binding ([$^3$H]-compound of formula (I)) using mouse spleen tissue WT FIG. 2 shows that specific binding in mouse spleen tissues of compound of formula (I) is saturable. The calculated half maximal affinity (Kd) is 0.58 nM for mouse CB2 receptors and the CB2 receptor expression level (Bmax) is 430 fmol/mg in mouse spleen tissue.

Figure 3:
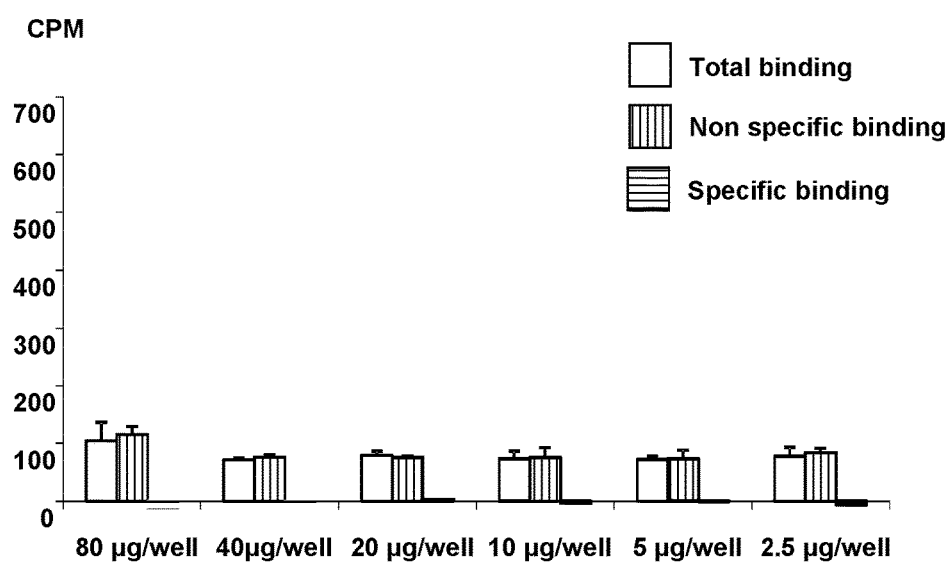

FIG. 3: Radioligand binding ($^3$[H]-compound of formula (I)) using mouse spleen KO (NIH)

FIG. 3 shows in contrast to FIG. 1 lack of specific binding of compound of formula (I) in mouse spleen tissues that were retrieved from CB2 deficient mice. Using increasing amounts of membranes, specific binding remains absent, indicating the high specific binding to CB2 receptors as demonstrated in mouse spleen tissues that were retrieved from wild type littermates.

We claim:

1. A compound of formula (I)

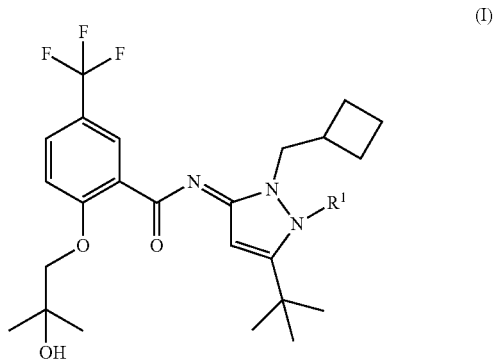

wherein R¹ is a methyl group and wherein at least one of the atoms of the methyl group of R¹ is replaced with a radionuclide independently selected from the group consisting of [³H], [¹¹C] and [¹⁴C].

2. The compound according to claim 1, wherein R¹ is C[³H]₃, [¹¹C]H₃ or [¹⁴C]H₃.

3. A pharmaceutical composition comprising a compound according to claim 1.

4. A process for the manufacture of a compound according to claim 1 comprising reacting a compound of formula (A)

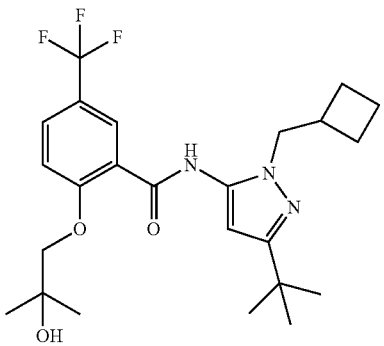

(A)

in the presence of [³H]-methyl 4-nitrobenzenesulfonate, [³H]-methyl iodide, [¹¹C]-methyl triflate, [¹¹C]-methyl iodide, [¹¹C]-methyl 4-nitrobenzenesulfonate, [¹⁴C]-methyl triflate, [¹⁴C]-methyl iodide or [¹⁴C]-methyl 4-nitrobenzenesulfonate.

5. The compound according to claim 1, wherein at least one of the hydrogen atoms of the methyl group of R¹ is replaced with [³H].

6. The compound according to claim 1, wherein the compound is (NE)-N-[5-tert-butyl-2-(cyclobutylmethyl)-1-(tritritiomethyl)pyrazol-3-ylidene]-2-(2-hydroxy-2-methylpropoxy)-5-(trifluoromethyl)benzamide, having the formula:

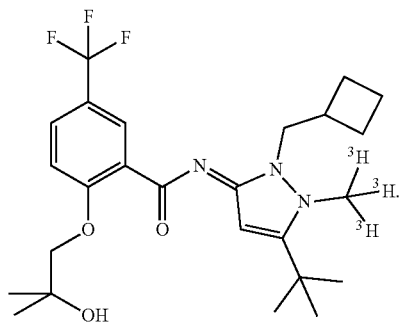

7. The compound according to claim 1, wherein the compound is (NE)-N-[5-tert-butyl-2-(cyclobutylmethyl)-1-([¹⁴C]methyl)pyrazol-3-ylidene]-2-(2-hydroxy-2-methylpropoxy)-5-(trifluoromethyl)benzamide, having the formula:

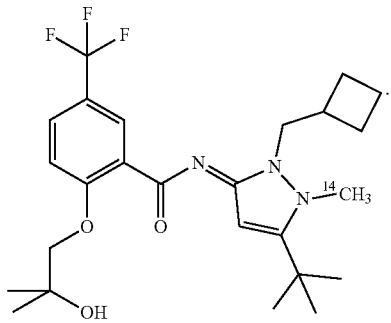 [SMILES: Cn1c(C(C)(C)C)c/c(=N\C(=O)c2cc(C(F)(F)F)ccc2OCC(C)(C)O)n1CC1CCC1]

8. The compound according to claim 1, wherein the compound is (NE)-N-[5-tert-butyl-2-(cyclobutylmethyl)-1-([¹¹C]methyl)pyrazol-3-ylidene]-2-(2-hydroxy-2-methylpropoxy)-5-(trifluoromethyl)benzamide, having the formula:

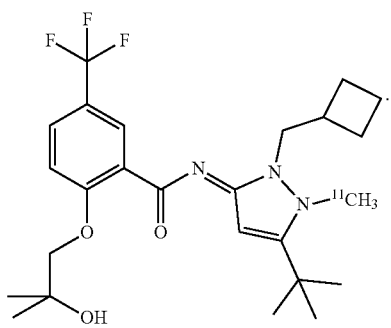 [SMILES: CC(C)(O)COc1ccc(C(F)(F)F)cc1C(=O)/N=c1\cc(C(C)(C)C)n([11CH3])n1CC1CCC1]

* * * * *